United States Patent
Dempster (10) Patent No.: US 10,501,320 B2
(45) Date of Patent: Dec. 10, 2019

(54) OZONE GENERATION SYSTEM

(71) Applicant: Pacific Ozone Technology, Inc., Benicia, CA (US)

(72) Inventor: Philip Tinsley Dempster, Concord, CA (US)

(73) Assignee: Pacific Ozone Technology, Inc., Benicia, CA (US)

( * ) Notice: Subject to any disclaimer, the term of this patent is extended or adjusted under 35 U.S.C. 154(b) by 28 days.

(21) Appl. No.: 15/136,526

(22) Filed: Apr. 22, 2016

(65) Prior Publication Data

US 2016/0311687 A1  Oct. 27, 2016

Related U.S. Application Data

(60) Provisional application No. 62/152,360, filed on Apr. 24, 2015.

(51) Int. Cl.

| | | |
|---|---|---|
| *C01B 13/11* | (2006.01) | |
| *A61L 2/26* | (2006.01) | |
| *A61L 2/20* | (2006.01) | |
| *A61L 9/015* | (2006.01) | |
| *C02F 1/78* | (2006.01) | |

(52) U.S. Cl.
CPC .......... *C01B 13/115* (2013.01); *A61L 2/202* (2013.01); *A61L 2/26* (2013.01); *A61L 9/015* (2013.01); *C02F 1/78* (2013.01); *C01B 2201/90* (2013.01); *C02F 2201/782* (2013.01)

(58) Field of Classification Search
CPC ... C01B 13/115; C01B 2201/90; C01B 13/11; C01B 2201/64; C01B 2201/76; C01B 13/10; C01B 2201/14; A61L 2/202; A61L 2/26; A61L 9/015; C02F 1/78; C02F 2201/782; B01J 4/008; B01J 2219/0805; B01J 19/088; B01J 2219/00038; B01J 2219/00162; B01J 219/00164
See application file for complete search history.

(56) References Cited

U.S. PATENT DOCUMENTS

| | | | | |
|---|---|---|---|---|
| 4,117,706 A | * | 10/1978 | Lami | ............. B21B 37/38 137/102 |
| 6,372,096 B1 | * | 4/2002 | Ditzler | ............. C01B 13/11 204/164 |
| 9,186,647 B2 | | 11/2015 | Okihara et al. | |
| 2012/0219460 A1 | * | 8/2012 | Okihara | ............. C01B 13/11 422/111 |

* cited by examiner

*Primary Examiner* — Xiuyu Tai
(74) *Attorney, Agent, or Firm* — Aka Chan LLP (57) ABSTRACT

An ozone generation system which is adaptable for supplying ozone to different medium and small application processes. The system has a source of feed gas, a corona discharge cell receiving the feed gas from the feed gas source and generating ozone for the application process, a flow controller measuring and managing the flow of the feed gas from the feed gas source to the corona discharge cell; and a regulator receiving gas from the corona discharge cell and sending the gas to the application process. The regulator maintains pressure in the corona discharge cell independent of the application process pressure.

28 Claims, 11 Drawing Sheets

OZONE GENERATION SYSTEM

CROSS-REFERENCE TO RELATED APPLICATIONS

This application claims the benefit of U.S. Provisional Patent Application No. 62/152,360, filed Apr. 24, 2015, which are incorporated by reference along with all other references cited in this application.

BACKGROUND OF THE INVENTION

This invention relates to ozone generation systems. There are many applications for ozone, including waste and water treatment, disinfection, cleaning, odor removal, extermination, and sterilization. Many ozone generation systems are very large, such as those for municipal waste and water treatment plants, and other ozone generation systems are smaller, such as systems for small industrial and domestic applications. The large ozone generators incorporate controls and features reflecting the significant investment in an industrial plant, while the controls and features of smaller ozone generation systems are limited.

Such smaller ozone generation systems typically comprise a source of feed gas, a device to control the flow of the feed gas with some device or technique to measure the feed gas flow, a plasma cell which generates the ozone from the feed gas, and a device to control the pressure in the plasma cell. The ozone generated is used in an application process. The feed gas may be compressed air, compressed air in which oxygen has been concentrated, or compressed oxygen. The device used to control the flow of the feed gas is normally a manually adjustable valve, and the device used to control the pressure in the plasma cell is an adjustable value at the output of the cell. To monitor the feed gas flow, a rotameter is typically used. The pressure in the cell is monitored by a mechanical gauge.

Unfortunately, in these ozone generation systems the flow and pressure setting are likely to be unstable. The application process pressure is generally quite variable and strongly affects the flow and pressure in the ozone generation system. Rotameters, which are often used for flow measurement due to their low costs, have poor dynamic range, poor resolution, and an undesirable dependency on pressure. Adjustments of the device to control the flow of feed gas and the pressure in the cell device are interdependent, making adjustment an art and not a procedure. These adjustments require the constant attention of a human technician skilled in the operation of that particular ozone generation system. Furthermore, the use of a rotameter and a pressure gauge requires that pneumatic plumbing be coupled to the control panel of the ozone generation system. It is preferable that an electrical control panel remain completely electrical. Additionally, the dependency of flow and cell pressure on the pressure of the application process itself is a major weakness in the system as described above.

A possible solution is to replace the rotameter with a flow controller which is readily available. Flow controllers comprise a flow measurement system, a proportional valve and a feedback system that controls the valve opening to achieve the desired flow control. A flow controller allows the molar flow to remain constant with changes in pressure. But a problem is that conventional flow controllers are expensive compared to a rotameter and a needle valve. Furthermore, a flow controller by itself cannot regulate ozone cell pressure. The ozone cell pressure will vary as a function of flow and as a function of the application process pressure. Therefore, a conventional flow controller is neither an economical solution nor a complete solution.

Therefore, there is a need for an ozone generation system which can accurately and controllably supply ozone to a medium or small scale application processes at a reasonable cost.

BRIEF SUMMARY OF THE INVENTION

Accordingly, the present invention provides for an ozone generation system for supplying ozone to an application process. The system has a source of feed gas, a corona discharge cell receiving the feed gas from the feed gas source and generating ozone for the application process, a flow controller measuring and managing the flow of the feed gas from the feed gas source to the corona discharge cell, and a regulator maintaining pressure in the corona discharge cell independent of pressure in the application process. The flow controller further includes a first valve controlling the flow from the feed gas source to the corona discharge cell, the valve responsive to electrical control signals; and an electronics system adjusting the valve to maintain a constant flow from the feed gas source to the corona discharge cell, the electronics system generating the electrical control signals responsive to calculations of flow of the feed gas through an orifice.

The present invention further provides for an ozone generation system for supplying ozone to an application process. The system has a source of feed gas, a corona discharge cell receiving the feed gas from the feed gas source and generating ozone for the application process, a flow controller measuring and managing the flow of the feed gas from the feed gas source to the corona discharge cell; and a regulator receiving gas from the corona discharge cell and sending the gas to the application process. The regulator further includes a block with an inlet for receiving gas from the corona discharge cell and an outlet for sending the gas to the application process, a flexible diaphragm disposed with respect to the block to cover the inlet and outlet; and a subsystem biasing the diaphragm against the inlet and outlet by gas pressure so that the pressure of the gas flow from the inlet to the outlet is controlled by the gas pressure of the subsystem against the diaphragm, whereby the regulator maintains pressure in the corona discharge cell independent of pressure in the application process.

The present invention also provides for an ozone generation system for supplying ozone to an application process. The system has a source of feed gas, a corona discharge cell receiving the feed gas from the feed gas source and generating ozone for the application process, a flow controller measuring and managing the flow of the feed gas from the feed gas source to the corona discharge cell; and a regulator receiving gas from the corona discharge cell and sending the gas to the application process. The regulator further includes a block with an inlet for receiving gas from the corona discharge cell and an outlet for sending the gas to the application process, the block having a chamber in pneumatic connection with the inlet, a flexible diaphragm disposed with respect to the block to cover the outlet and the chamber; and a sliding piston biasing the diaphragm against the outlet so that pressure of the gas in the chamber from the inlet on one side of the diaphragm and the bias of the sliding piston and ambient pressure on an opposite side of the diaphragm controls the pressure of the gas flow from the inlet to the outlet, whereby the regulator maintains pressure in the corona discharge cell independent of application process pressure.

Other objects, features, and advantages of the present invention will become apparent upon consideration of the following detailed description and the accompanying drawings, in which like reference designations represent like features throughout the figures.

BRIEF DESCRIPTION OF THE DRAWINGS

It should be noted that at times the same reference numerals are used in the different figures in the drawings to designate elements which have similar or identical functions to aid the understanding of the reader.

DETAILED DESCRIPTION OF THE INVENTION

Figure 1:
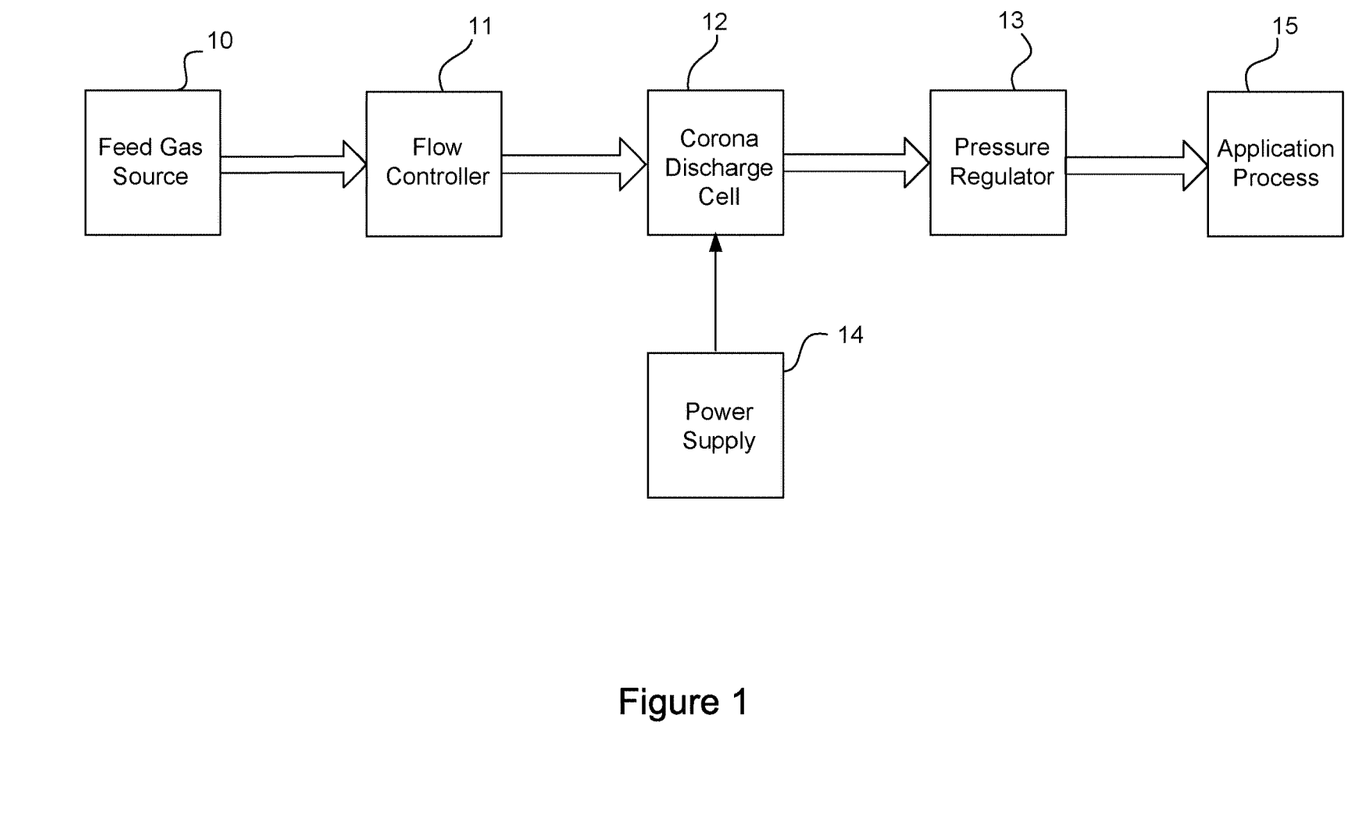
FIG. 1 shows the general organization of an ozone generation system according to one embodiment of the present invention.

The present disclosure generally relates to ozone generation systems of moderate size which can be manufactured at relatively low cost. As described below, these ozone generation systems operate accurately under easy operator control. FIG. 1 shows the general organization of such an ozone generation system for an application process 15 according to one embodiment of the present invention. The system has a source 10 of feed gas which supplies the feed gas to a corona discharge cell 12 through a flow controller 11. Besides oxygen, the feed gas may be air which, of course, contains oxygen. A power supply 14 allows the cell 12 to generate ozone for the application process 15 through a pressure regulator 13 which maintains the proper pressure for the cell 12 independent of the back pressure from the application process 15 and relatively independent of the rate of gas flow. It should be noted that pneumatic flows in the drawings are indicated by broad arrows and electrical connections are indicated by lines or linear arrows.

Flow Controller

Figure 2:
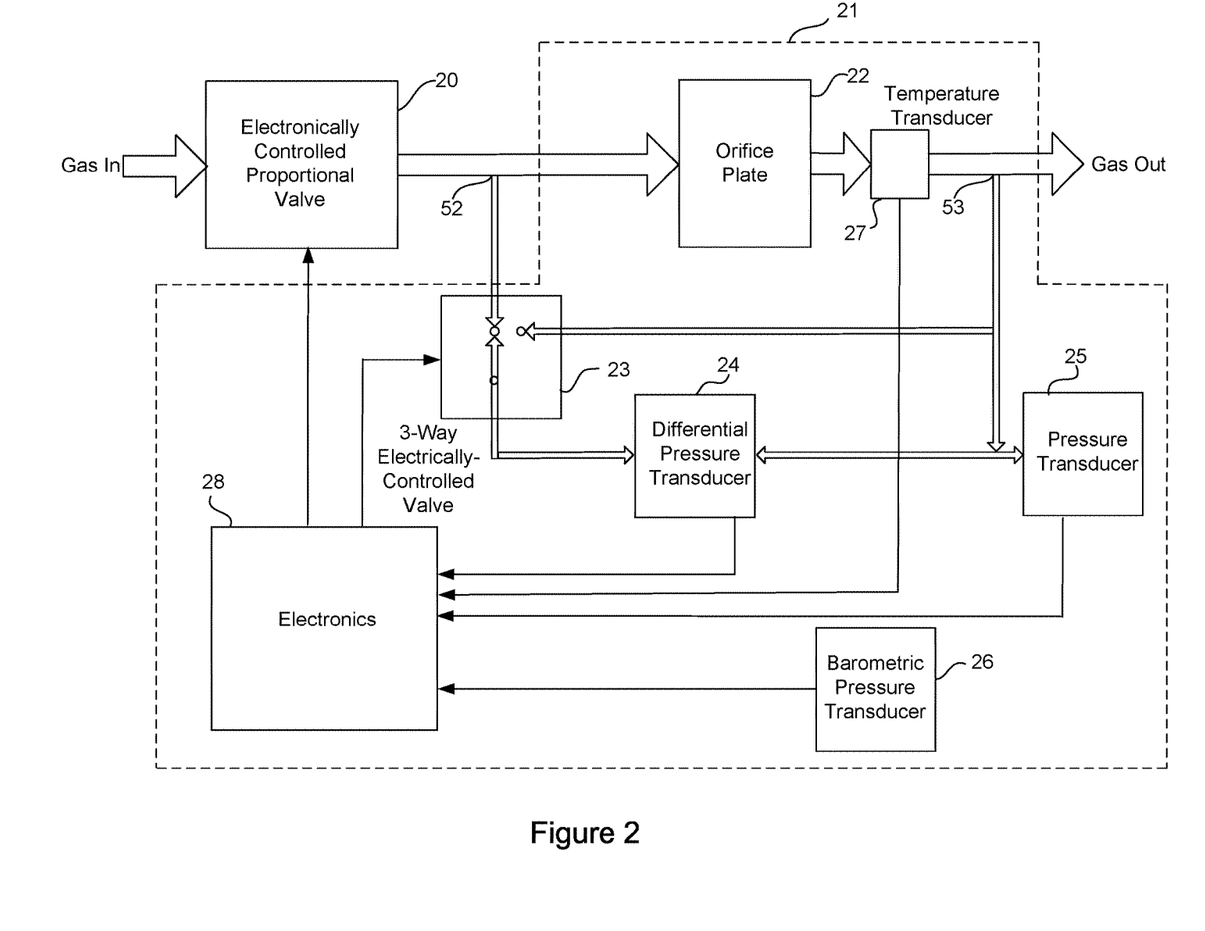
FIG. 2 shows the general organization of a flow controller in the FIG. 1 ozone generation system.

The flow controller 11 of the ozone generation system proportionally controls the rate of oxygen (or air) delivery to the cell 12 to ensure efficient ozone production. The controller 11 includes a valve 20 and a flow sensing unit 21, as illustrated by FIG. 2. Feed gas flow is controlled by the valve 20. The flow sensing unit 21 determines the flow through the valve 20 and controls the valve 20 to maintain the flow in a feedback loop. The elements of the flow sensing unit 21 are enclosed by a dotted line in the drawing to distinguish it from the valve 20; it should be understood that elements of the flow sensing unit are distributed with other elements over the ozone generation system.

The flow sensing unit 21 has an orifice plate 22, a 3-way electrically-controlled valve 23, a differential pressure transducer 24, a pressure transducer 25, a barometric pressure transducer 26, a cell temperature transducer 27 and an electronics control 28. The orifice plate (or block) 22 determines the flow of the gas by the well-known Bernoulli principle. Orifice plate is used in a general sense of an element having an orifice in a gas flow. Gas stream flowing through an orifice exhibits a predictable pressure drop that is a function of flow rate, gas composition, absolute temperature, absolute pressure, and dimensions of the orifice. Pneumatic junctions 52 and 53 provide access to the gas stream flow before and after the orifice plate 22 to the differential pressure transducer 24 and pressure transducer 25. The differential pressure transducer 24 determines the differential pressure across an orifice in the orifice plate 22 through the 3-way valve 23. A more detailed description of the 3-way valve 23 is found below. Barometric pressure transducer 26 measures the ambient pressure. The addition of barometric pressure to gauge pressure as measured by transducer 25 yields absolute gas pressure in the orifice in the plate 22.

The temperature transducer 27 measures the temperature of the flow in the vicinity of the orifice plate 22. Low-cost devices for the pressure transducers 24-26 are readily available as well as for the temperature transducer 27. These transducers 24-27 supply their measurements to the electronics 28 which calculates the flow of the feed gas through the orifice plate 22. The electronics 28 are part of the system controller described below of the ozone generation system.

The flow of the gas through the orifice in the plate 22 can be approximated well by the equation:

$$F = K\sqrt{(DP*P)/T}$$

where F is the flow, DP is the pressure drop across the plate orifice (i.e., the pressure differential upstream and downstream of the orifice), P is the absolute pressure, T is the absolute temperature and K is a scaling constant that depends on gas composition and dimensions of the orifice. If it is assumed that the gas composition from the feed gas source 10 is fixed (e.g., 95% $O_2$ and the balance $N_2$), and it is assumed that the dimensions of the orifice in the orifice plate 22 are fixed, the K may be adjusted empirically by comparison with a reference flow.

The electrical analog signals for P, DP and T may be converted by an analog-to-digital converter to become numerical values available to a microprocessor-based calculation engine in the electronics 28. P, DP and T may also have direct numerical output to the microprocessor-based calculation engine. The microprocessor calculates Equation 1 above, and routines may be run that allow for calculation and storage of K to be compared with a known reference flow. It is to be understood that F can be calculated by other techniques, such as with analog circuitry. The K value may be stored, for example, as an adjustment of a trimpot.

Once F is calculated, F is compared with a desired flow rate. A desired flow rate may be a numerical value, or the desired flow rate may be an analog value derived from an operated adjustment or an external source. The desired flow rate may be fixed or variable. Given the desired flow rate and F, a standard PID servo may be implemented to drive the valve 20 that controls the flow. Such a valve may be a stepper motor coupled to a needle valve, a magnetically driven proportional orifice, a proportional spool valve, a duty-cycle controlled valve, or in fact any kind of valve capable of adjusting average flow in a proportional fashion. This operation is cyclically repeated to control the gas flow as desired. Common digital electronics provides a flow control duty cycle of about 0.2 seconds.

A practical difficulty of the system described above is that the flow F is proportional to the square root of DP or stated in another way, DP is proportional to $F^2$. Suppose that the F flow measurement must work over a 10-1 dynamic range with an accuracy of 5% of reading. For simplicity of illustration, units are chosen so that at full scale flow is F=1, and differential pressure DP=1. If the flow decreases so that F=0.1, DP should be 0.01 due to the square law relationship of DP as a function of F. To maintain an accuracy of 5% of the reading at F=0.1, DP must be known within the range of 0.009-0.011. This implies a baseline accuracy to be maintained at a level of 0.01%. In general, such a level of performance is not available in a pressure transducer of reasonable cost.

Nonetheless the flow sensing unit 21 achieves the required level of baseline accuracy with low-cost transducers. The electrically controlled, three-port valve 23 connects in effect the two inputs of the differential pressure transducer 24 together at intervals, which implies that the pressure transducer 24 is presented with a zero pressure differential input. After some time to allow the pressure measurement to settle, the observed pressure signal from the transducer 24 is measured and the value stored. Since that signal corresponds to a pressure of zero, its stored value is subsequently subtracted from the pressure signal to achieve high baseline accuracy.

The baseline offset does not remain constant over changes in time and temperature and this recalibration operation is repeated at regular intervals. Because it is necessary to suspend measurement during these baseline accuracy calculations, it is desirable to perform the calculation sufficiently fast so as to not disturb flow regulation and flow measurement operations. To achieve the required speed, the 3-way valve 23 is a fast-acting valve with minimal pumping, short, low volume pneumatic connections. A suitable valve is EVO-3-24 3-way valve from Clippard Instrument Laboratory of Cincinnati, Ohio. The pressure transducer 24 is likewise fast-responding. The brief periods of data extraction from the flow record may be filled with the last flow calculated and the operation of flow control assumes that the measured flow is the same as the last valid measurement. Alternatively, regulation of flow can be interrupted, i.e., control is frozen in place, during this recalibration period. In practice, this presents no problems since the recalibration can be performed quickly relative to the flow control duty cycle. To maintain a frequency response of X Hz by the flow controller 11 and its flow sensing unit 21, the zero-measuring period should last less than 0.25/X.

Figure 3:
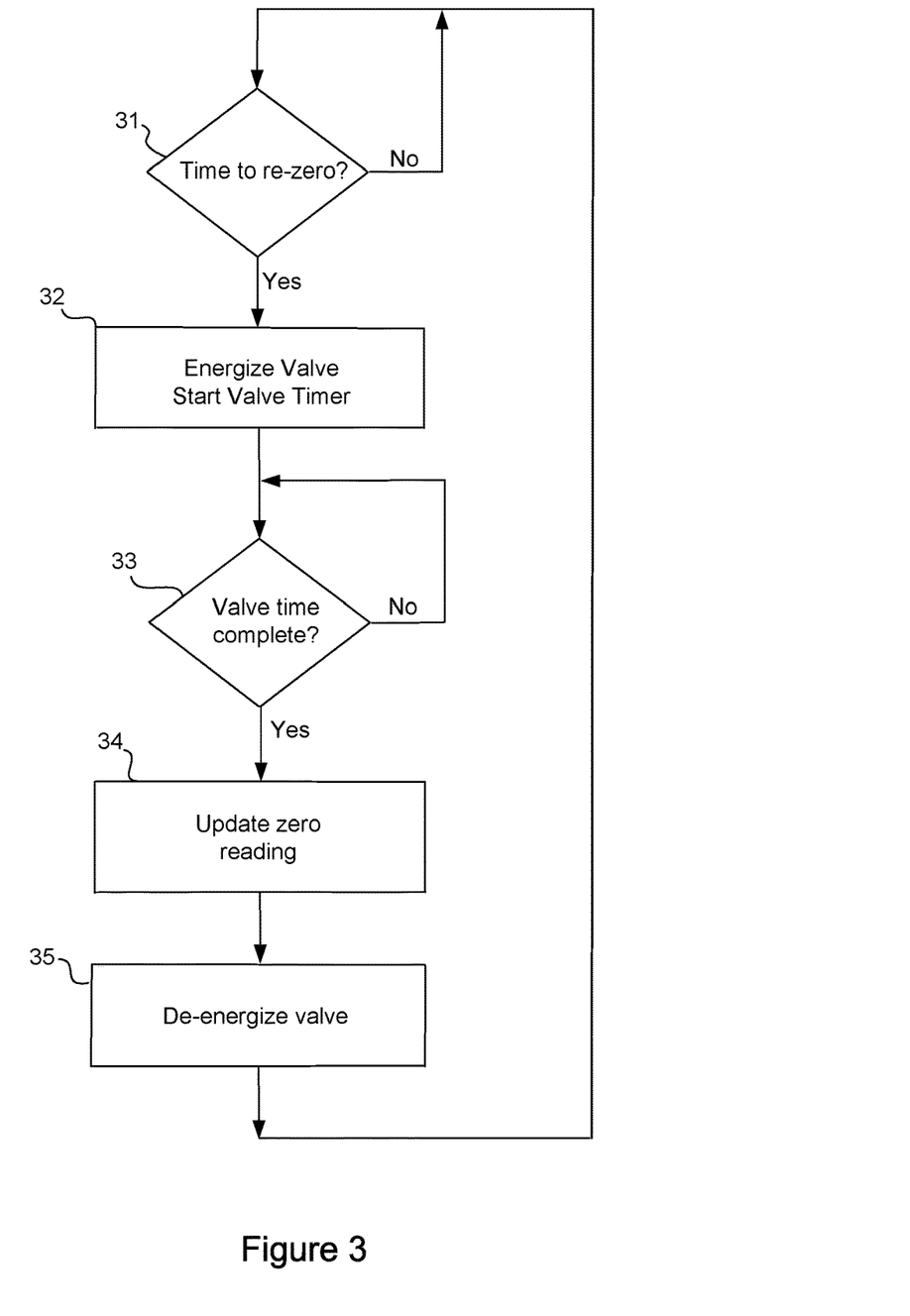
FIG. 3 shows an operational flow chart of steps by which the electronics control in the FIG. 2 flow controller periodically recalibrates a pressure baseline for accurate pressure measurements.

FIG. 3 is a flow chart of the recalibration operation including its timing with respect to normal operations. After initialization steps have been performed and the flow sensing unit 21 is in normal operation, the recalibration operation operates in a loop with a recalibration timer. Step 31 determines whether recalibration can be performed. The ozone generation system may be performing an operation requiring the 3-way valve 23. If the time for recalibration is not appropriate, the recalibration process flow loops back to the step 31 again. When the recalibration can be performed, the process flow moves to step 32 at which time the valve 23 is energized so that the two inputs to the differential pressure transducer 24 are connected so that the transducer should read a nominal pressure of zero. The valve recalibration timer is also started. Timing step 33 allows sufficient time for the pressure measurement by the transducer 24 to settle. After recalibration timer indicates that sufficient time has passed, the reading by the transducer 24 is uploaded for the new zero pressure reading by step 34. The valve 23 is de-energized in step 35 and returns to normal operations. The recalibration process flow returns to step 31.

Figure 7:
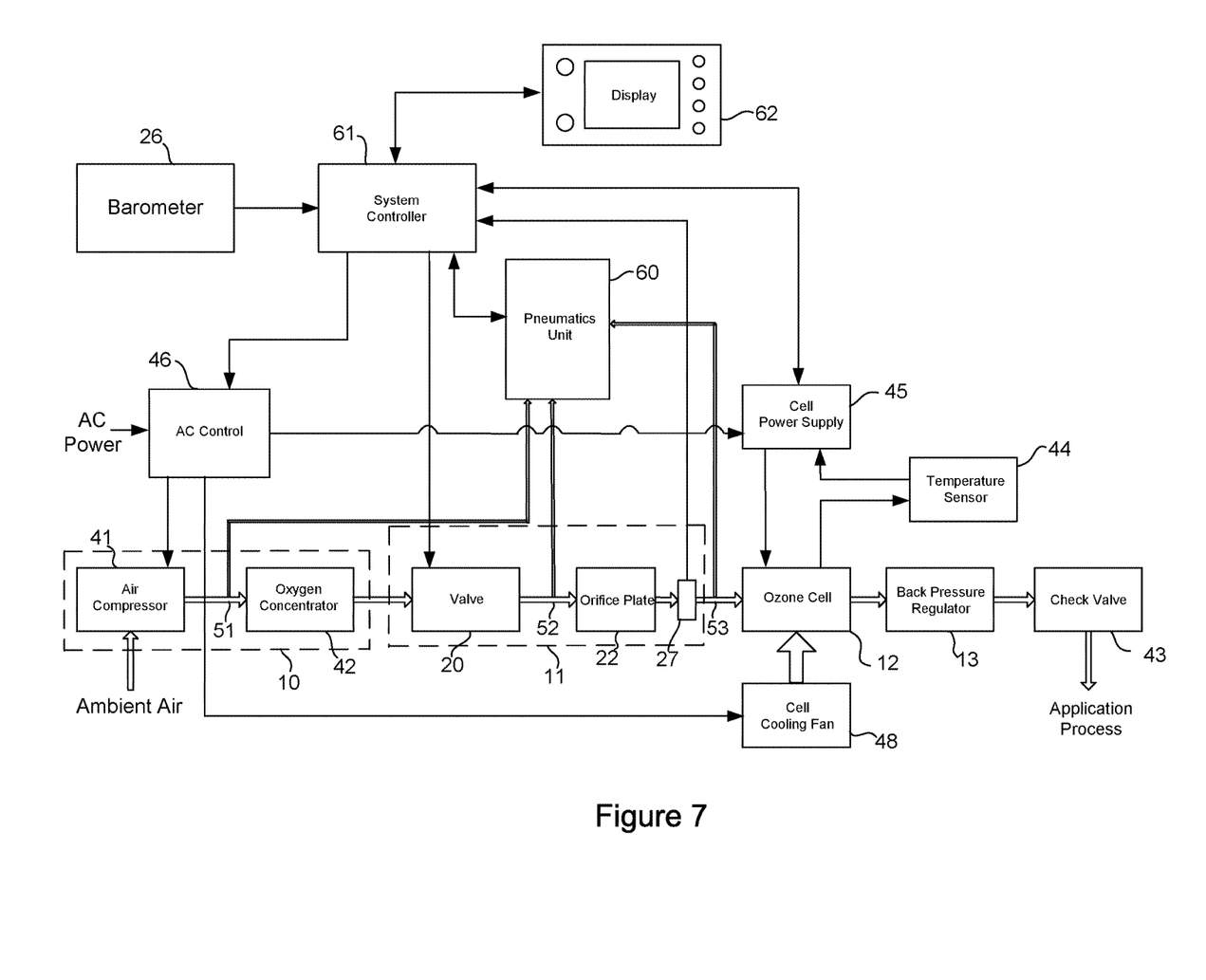
FIG. 7 is a schematic illustration of an overall ozone generation system according to one embodiment of the present invention.

If the flow control is by digital manipulation in a microprocessor, a display, such as shown in FIG. 7, may also be addressed to indicate measured flow. A system of buttons or controls may be used to set the desired flow, or desired flow may be a fixed value.

Pressure Regulator

As stated earlier, previous efforts to establish and maintain the proper pressure in the corona discharge cell 12 have been problematic even with regulated flows. Typically a needle valve or its equivalent has been used with human intervention to maintain the proper cell pressure. For example, with changes in the flow setting or application process pressure, the cell pressure also changes. A needle valve could be adjusted by the human operator to compensate for the changes to maintain the proper pressure in the corona discharge cell 12. But a human must watch the ozone generation process to handle any required "tweaking" of the needle valve.

Figure 4:
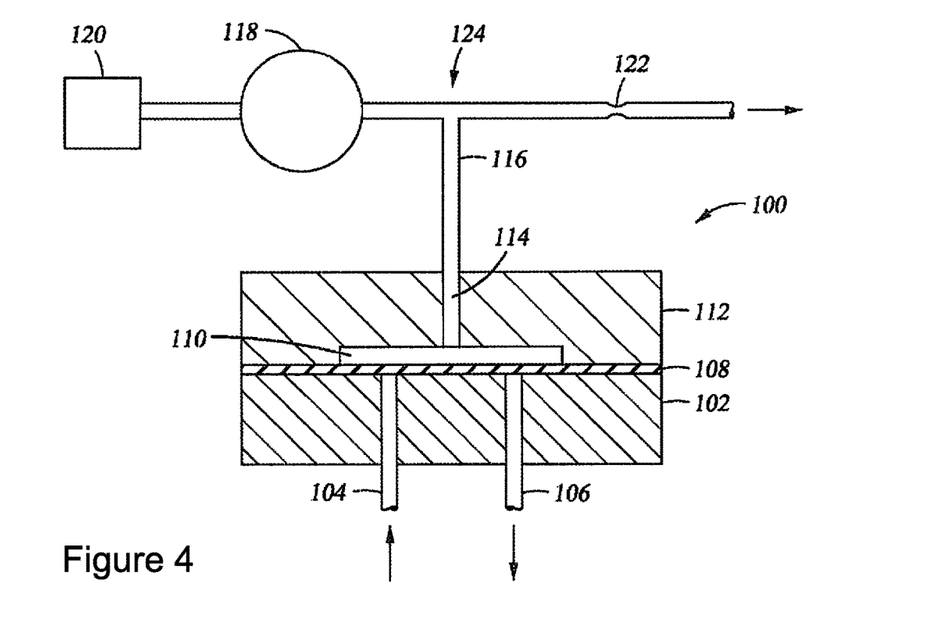
FIG. 4 is a schematic illustration of a valve according to one embodiment of the present invention.

To address this problem, the present invention provides a valve that automatically regulates the pressure at the valve inlet for the pressure regulator 13 and the pressure is relatively independent of the process gas flow. FIG. 4 is a schematic illustration of a valve according to one embodiment of the present invention. The valve 100 includes a plate 102 with two holes 104, 106 which respectively function as an inlet for the gas from the corona discharge cell 12 and an outlet to the application process as represented by the square 15 in FIG. 1. A flexible diaphragm 108 disposed across the plate 102 covers the holes 104, 106. A small chamber 110 is formed on the side of the diaphragm facing away from the holes 104, 106 in an upper plate 112. A gas under pressure R is introduced into the small chamber 110 through a second input port 114 connected to a gas feed tube 116. The gas feed tube 116 forms the base of a "T" junction which has one arm connected to a compressed air source 120 and a conventional pressure regulator 118. The second arm of the "T" junction is connected to a small orifice 122 leading to the ambient atmosphere to allow the air under pressure R to leak into the atmosphere. A pressure at the inlet hole 104 does not result in gas flow until the inlet pressure equals or exceeds R and pressure at the outlet hole 106 has no effect on the pressure at which flow begins, unless the outlet pressure approaches or exceeds the inlet set pressure.

Figure 5:
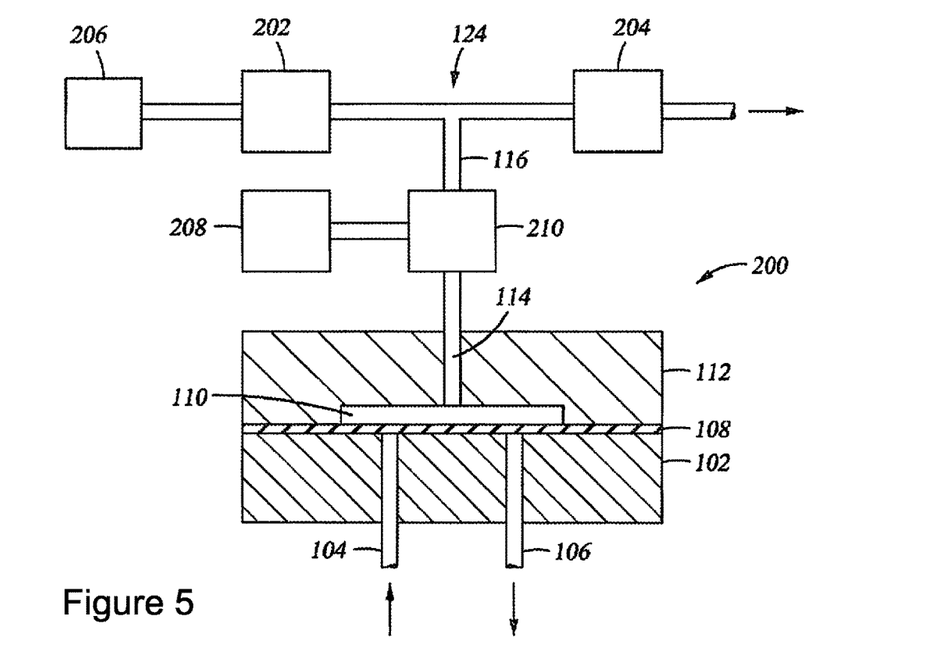
FIG. 5 is a schematic illustration of a valve according to another embodiment of the present invention.
Figures 6A, 6B, 6C:
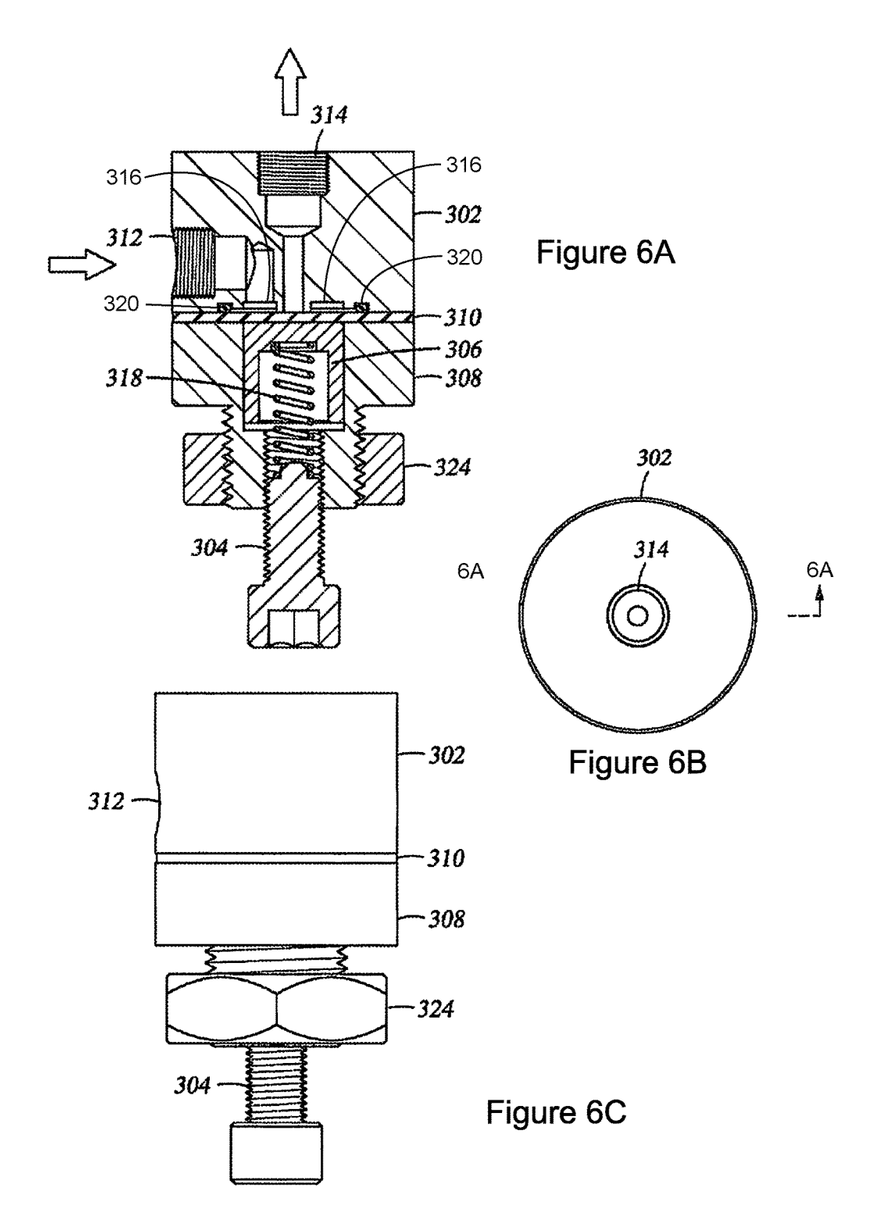
FIGS. 6A-6G are different views of a valve according to another embodiment of the present invention.
Figures 6D, 6E, 6F:
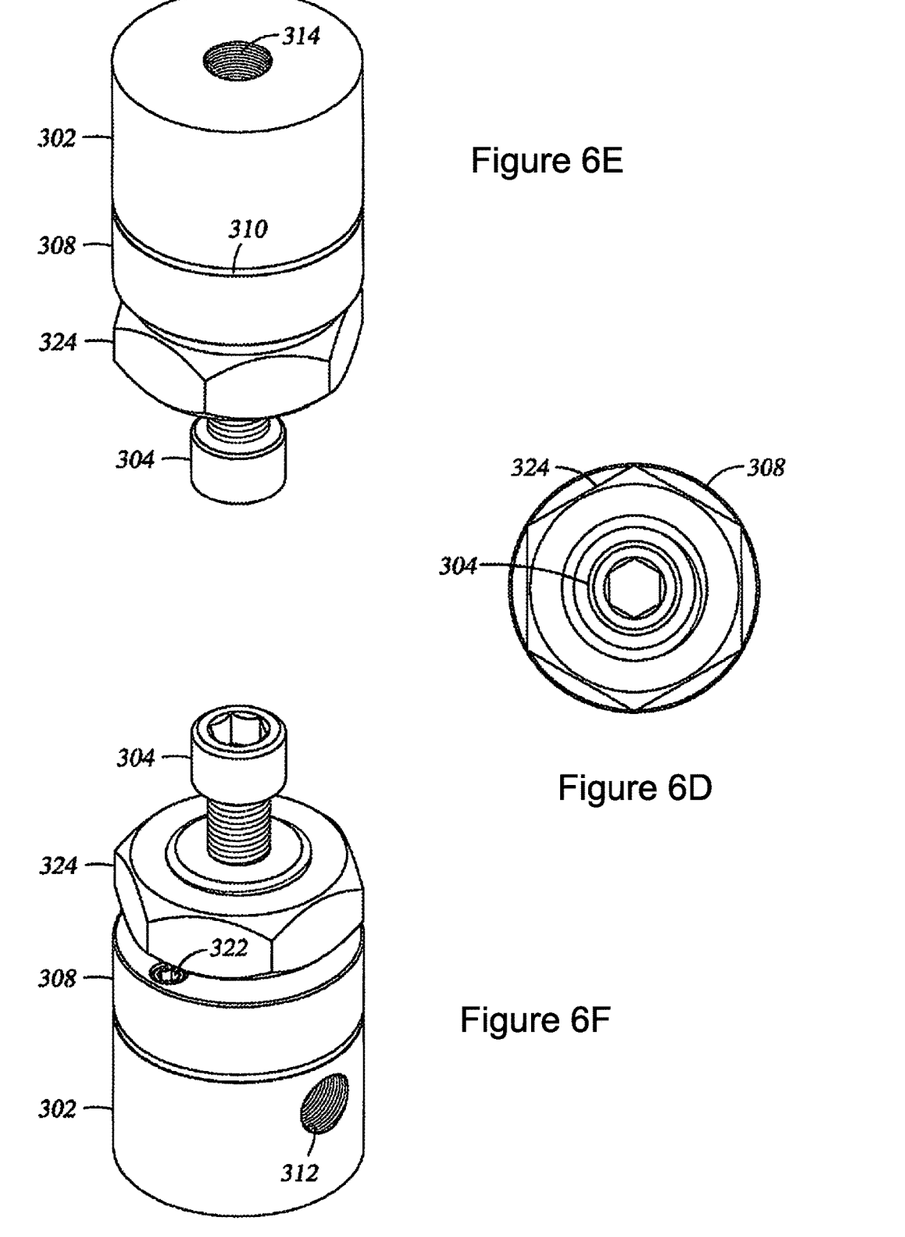
Figure 6G:
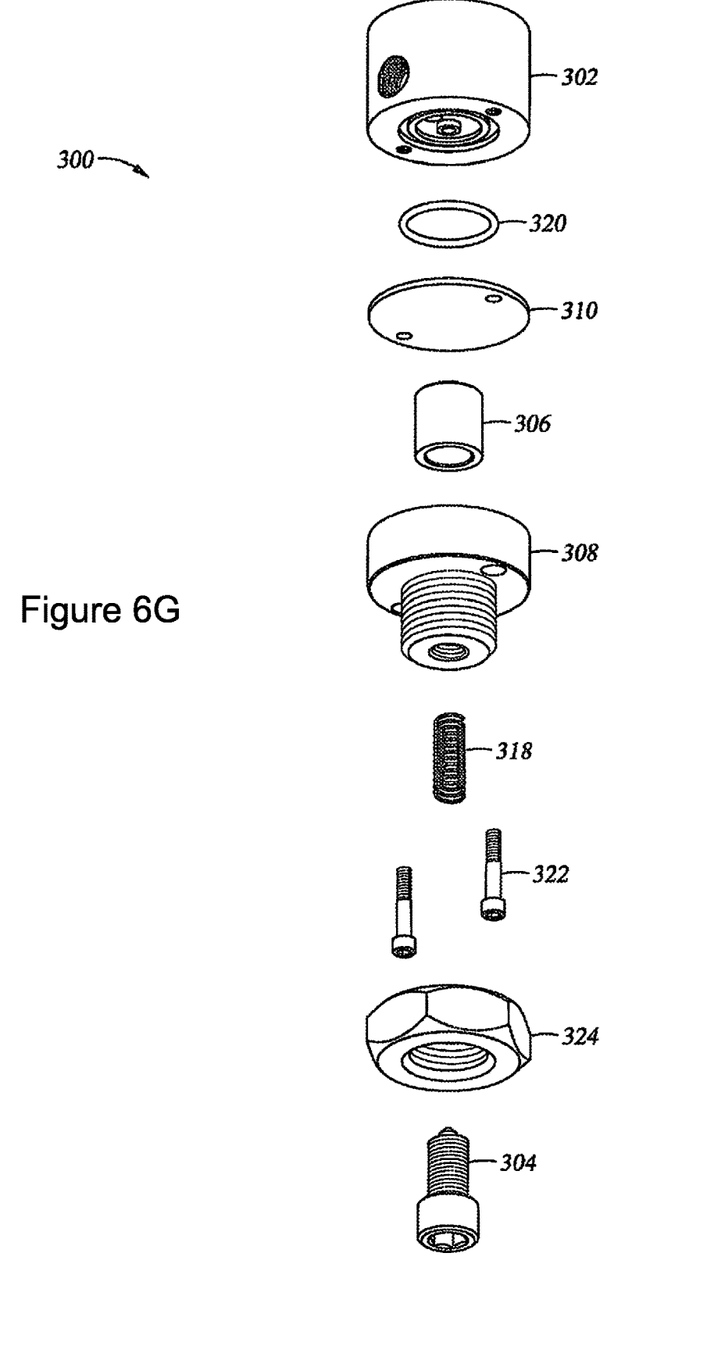

FIG. 5 is a schematic illustration of a valve 200 according to another embodiment. The valve 200 is similar to valve 100, except that valve 200 establishes pressure in the small chamber 110 in a different manner. Specifically, the pressure regulator 118 and small orifice 122 of FIG. 4 are replaced with two valves 202, 204. The valve 202 is connected to a source 206 of pressurized gas, while the valve 204 is connected to the ambient atmosphere. A pressure transducer 208 measures the pressure in a second chamber 210 which is connected to the small chamber 110. The transducer 208 reads the pressure in the chamber 110 through the measurement of the pressure in chamber 210. If the pressure in the chamber 210 (and chamber 110) exceeds a set point by even a small margin, the valve 204 opens until the pressure in the chambers 110, 210 reaches the set point. Similarly, if the pressure is below the set point by even a small margin, the valve 202 opens to connect the source 206 to the chamber 110, 210 until the pressure reaches the set point.

Several variants are possible. For example, one of the valves 202, 204 may be replaced by a small orifice. In another example, one of the valves 202, 204 may be replaced by an orifice and the other valve 202, 204 is a proportional valve. In yet another example, the pressure transducer 208 may be connected directly to the input port 114 and the second chamber 210 eliminated. In still another example, two pressure transducers may be used with a first pressure transducer connected to the small chamber 110 and the other pressure transducer connected to the input port 114. In such a situation, regulation is obtained by the transducer at the input port 114, but the second transducer is used to set limits on the pressure in the small chamber 110.

FIGS. 6A-G are schematic illustrations of a valve 300 according to another embodiment for the pressure regulator 13 of FIG. 1. The valve 300 has a valve body 302, adjustment screw 304, piston 306, head 308, diaphragm 310, inlet 312 for the gas from the corona discharge cell 12 and outlet 314 for the gas to the application process 15. The piston 306 is spring-loaded and slides in the head 308, and the flexible diaphragm 310 covers the piston 306. Not shown in the drawings is a hole in the head 308 so that the diaphragm on the side of the piston 306 is exposed to the ambient. If pressure in the annular upper chamber 316 exceeds the force of the spring 318 divided by the area of the piston 306 and ambient pressure, the piston 306 will slide and open a space between the diaphragm 310 and the outlet 314. The consequent establishment of flow tends to reduce pressure at the inlet 312. The adjustment screw 304 may be used to adjust the force of the spring 318, and hence the inlet pressure. As in the cases described above, the application process pressure and the process gas flow has relatively little effect on the inlet pressure required to open the valve 300. An O-ring 320, assembly screws 322 and a mounting nut 324 are all used to assemble the valve 300.

Expanded Description of Overall System and Other Elements

FIG. 7 is a block illustration of the expanded description of the ozone generation system of FIG. 1, according to one embodiment of the present invention. Some of the elements of the FIG. 1 organization are indicated by dotted lines in FIG. 7.

An air compressor 41 and $O_2$ concentrator 42, which is a commercially available device and operates on a swing pressure molecular sieve principle, represent the feed gas source 10 of FIG. 1. The flow controller 11 has the proportional electrically-controlled valve 20 regulating gas flow from the oxygen concentrator 42. The orifice plate 22 receives the gas flow from the valve 20. The flow sensing unit 21 of which the orifice plate 22 is part has many of its elements included in a pneumatics unit 60. The unit 60 has a circuit board which includes a pressure measuring transducer that measures the output pressure of compressor 41 through pneumatic junction 51, the differential pressure transducer 24 which measures the pressure drop across the orifice in the orifice plate 22 through pneumatics junctions 52 and 53, an electrical input for the temperature transducer 27 that measures the temperature of the orifice plate 22 and hence temperature of the gas passing through the plate's orifice. The corona discharge cell 12 receives the gas flow from the orifice plate 22 and the back pressure regulator 13 establishes a controlled pressure in the ozone cell 12. An optional check valve 43 may be used to protect the ozone generating system from contamination or back flow from the application process. A fan 48 provides cooling air to the ozone cell 12.

Power is supplied to the air compressor 41 by an AC (Alternating Current) control unit 46 which also supplies power to a cell power supply 45 and the cell cooling fan 48. The cell power supply 45 supplies power to the corona discharge cell 12 and the fan 48 supplies air to cool the cell 12. A temperature transducer 44 monitors the temperature of the cell 12 and is connected back to the cell power supply 45 to turn off power to the cell 12 to avoid overheating the cell.

The ozone generation system is controlled by an electronic system controller 61 which is used for operator control, orchestration and control of the various functions, some of which have been described, of the ozone generation system. The system controller 61 includes the electronics 28 of FIG. 2 and performs the previously described calculations for the flow controller operations. The system controller 61 receives electrical input from the barometric temperature transducer 26, the pneumatics unit 60, the ozone cell power supply 45, and a display unit 62 which includes pushbuttons. The system controller 61 sends control signals to the AC control unit 46, the valve 20, the pneumatics unit 60 and the display unit 62 which provides an operator interface to the system controller 61. Through the AC control unit 46 the system controller 61 can switch on and off the AC line power to the ozone cell power supply 45, the cell cooling fan 48, and the air compressor 41.

The system controller 61 turns on the compressor 41 by means of the AC control unit 46. Gas begins to flow. The flow rate of gas (predominantly $O_2$) into the corona discharge cell 12 is regulated to a desired value as described above. The system controller 61 turns on and sets power in the ozone power supply 45. Ozone begins to emerge from the cell 12. The system controller 61 also turns on the cooling fan 48 in order to carry heat away from cell 12. Pressure in the cell 12 is established by the back pressure regulator 13 as described above.

The system controller 61 operates the various components sequentially. For example, air flow is established and verified before power is applied to the corona discharge cell 12. If the cell 12 is on and to be turned off, power may be removed from the cell 12 but gas allowed to flow in order to flush out residual ozone. If operating, power may be turned off if the cell 12 is too warm, there is loss of air flow, or inappropriate pressures are encountered. The system controller 61 computes the time of use of the cell 12 for service purposes, and logs events, such as incorrect air pressure, power, flow, or cell pressure.

Figure 8:
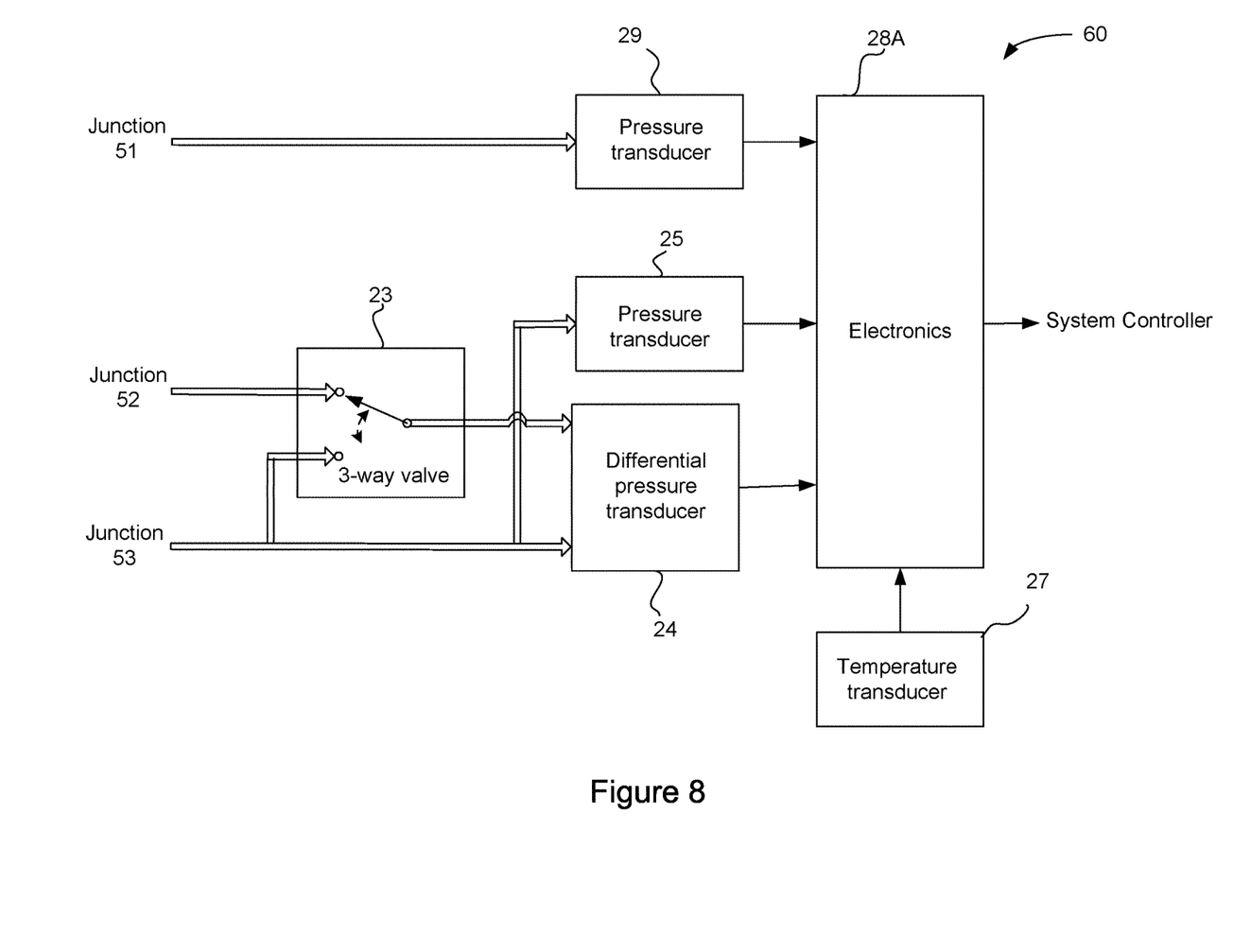
FIG. 8 is a schematic illustration of the pneumatics unit of FIG. 7 ozone generation system.

FIG. 8 is a more detailed illustration of the pneumatics unit 60 which provides an interface between the gaseous and electrical facets of the ozone generation system according to one embodiment of the present invention. The pneumatics unit 60 includes the three pressure transducers 24, 25, and 29 described with respect to FIG. 2, and electronics 28A receiving the electrical signals from the transducers 24, 25 and 29. The suffix "A" denotes that the electronics 28A is not the exactly same as the electronics 28 of FIG. 2, which includes portions of the system controller 61. The system controller 61 includes a microprocessor, computer memory and the program instructions described to perform the calculations previously described with respect to FIG. 2.

The transducer 29 is a gauge type of a range suitable to measure pressure of the compressor 41. Typically, the full scale range of transducer 29 is 30-150 psi. The transducer 25 is a gauge type for measuring pressure in the ozone cell 12.

Typically, the full scale range of transducer 25 is 10-30 psi. The differential pressure transducer 24 measures the pressure drop across the orifice in the orifice plate 22. Typically, the full scale range for the transducer 24 is 0.5-3 psi. As described earlier, the 3-way valve 23 allows the two inputs of the transducer 24 to be tied together under electrical control from the system controller 61, i.e., both inputs to the transducer are connected to the pneumatic junction 53 (located after the orifice plate 22). This allows the offset of transducer 24 to be measured under conditions of 0 pressure input. Otherwise, the valve 23 directs the pneumatic pressure from the junction 52 (located before the orifice plate 22) to the differential pressure transducer 24 which then receives the pneumatic pressures before and after the orifice plate 22. The temperature transducer 27 converts the temperature of the orifice plate 22 to an electrical signal.

Figure 9:
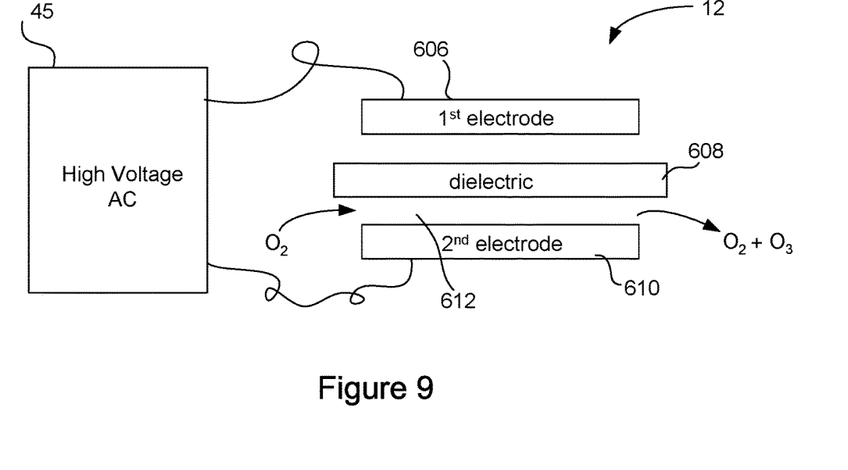
FIG. 9 is a schematic illustration of a corona discharge cell and its power supply of the ozone generation system according to one embodiment of the present invention.

FIG. 9 shows the corona discharge cell 12 and its AC high voltage power supply 45. The corona discharge cell 12 comprises a first electrode 606, a dielectric material 608, a second electrode 610, and a gap 612 formed between the dielectric material 608 and electrode 610. Diatomic Oxygen ($O_2$) is introduced into the gap 612, and AC voltage is applied between the electrodes 606, 610 to produce a corona discharge in the gap 612. The discharge splits molecules of $O_2$, and some atoms recombine into ozone ($O_3$).

Figure 10:
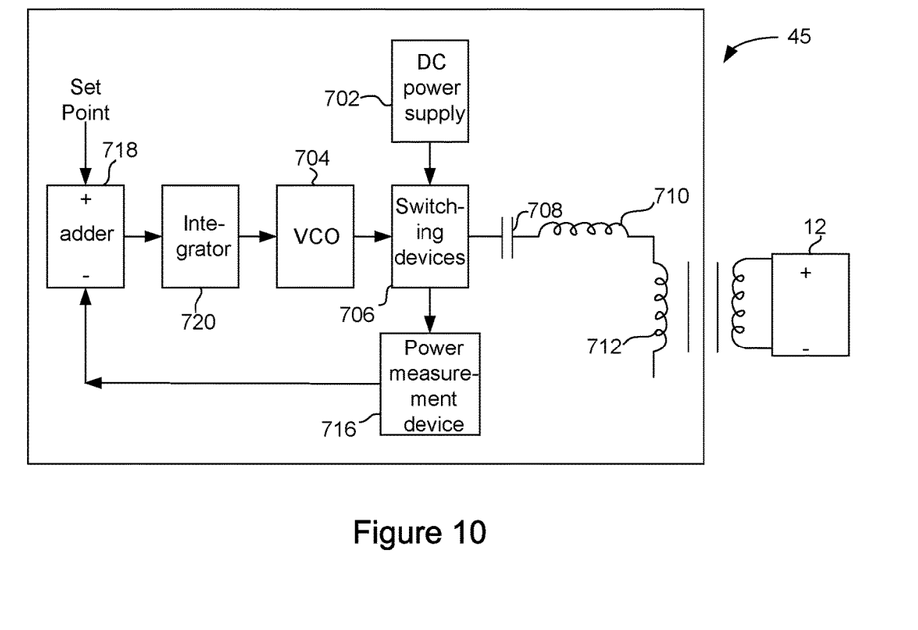
FIG. 10 is a schematic illustration of the FIG. 9 power supply.

FIG. 10 shows in detail the power supply 45 for the ozone cell 12. The power supply 45 has a DC power supply 702; AC power is converted to a fixed, regulated DC voltage according to well-known means. For example, a boost type power factor correction system may be used. Voltage-controlled oscillator (VCO) 704 controls power to switching devices 706. The action of switching devices 706 chops the DC voltage into a square wave. The output of switching devices 706 passes through a capacitor 708 which blocks any DC component of the output. The square wave voltage is applied to the first lead of an inductor 710 whose second lead is applied to the primary of step-up transformer 712. The secondary of the transformer 712 is applied to the ozone cell 12. Voltage and current in the primary coil of transformer 712 is controlled by varying frequency of the VCO 704. At high frequency, impedance of an inductor does not allow the passage of much current. Current, and therefore voltage, are held at a low value. As frequency is lowered, the inductance offers less impedance, and voltage and current increases.

Voltage and current increases to a maximum if the network comprising the inductor 710 and transformer 712 resonates with the electrical capacitance of the cell 12. In this embodiment, frequency is restrained to be greater than, or equal to, the resonant frequency. The rate of energy delivery is measured in a power measurement device 716. In this embodiment, the rate of energy delivery is represented by the average DC current supplied to the switching devices 706. Voltage need not be measured, because voltage is regulated to a fixed value. As a consequence, voltage may be considered to be a fixed, scaling quantity, not a variable. In this embodiment, input set point is a voltage. The difference of input voltage and power is derived in an adder 718. That difference is applied to the input of an integrator 720. The output of integrator 720 controls frequency of VCO 704. The VCO 704 controls the operation of the switching devices 706. If power is greater than the set point, the error is integrated in a sense that increases frequency, decreasing the delivered power. If power is less than the set point, the error is integrated in a sense that decreases frequency, increasing delivered power. In one embodiment, it is contemplated that the rate of energy delivery may be accomplished by averaging all of the instantaneous products of voltage and current over time.

In another embodiment, the functional components of the previous embodiment are the same, but certain parts are replaced by numerical techniques. In particular, variable frequency is produced by numerical techniques in a microprocessor. Power measurement is digitized by an analog-to-digital converter. Input setting is numerical, or it may be analog and then be converted to a digital form. The difference of setting and measured power is performed digitally. Their difference (i.e., error) is digitally integrated, and that number used in the routine that produces the variable frequency output to the switching devices.

In still another embodiment, frequency is not the primary method of control of output. Instead, a pulse width modulation system is used in combination with a choke at the output. It will be recognized by those skilled in the art that this is similar to a class D audio amplifier. It will be recognized by those skilled in the art that many other control systems would be possible without departing from the spirit of the invention.

Figure 11:
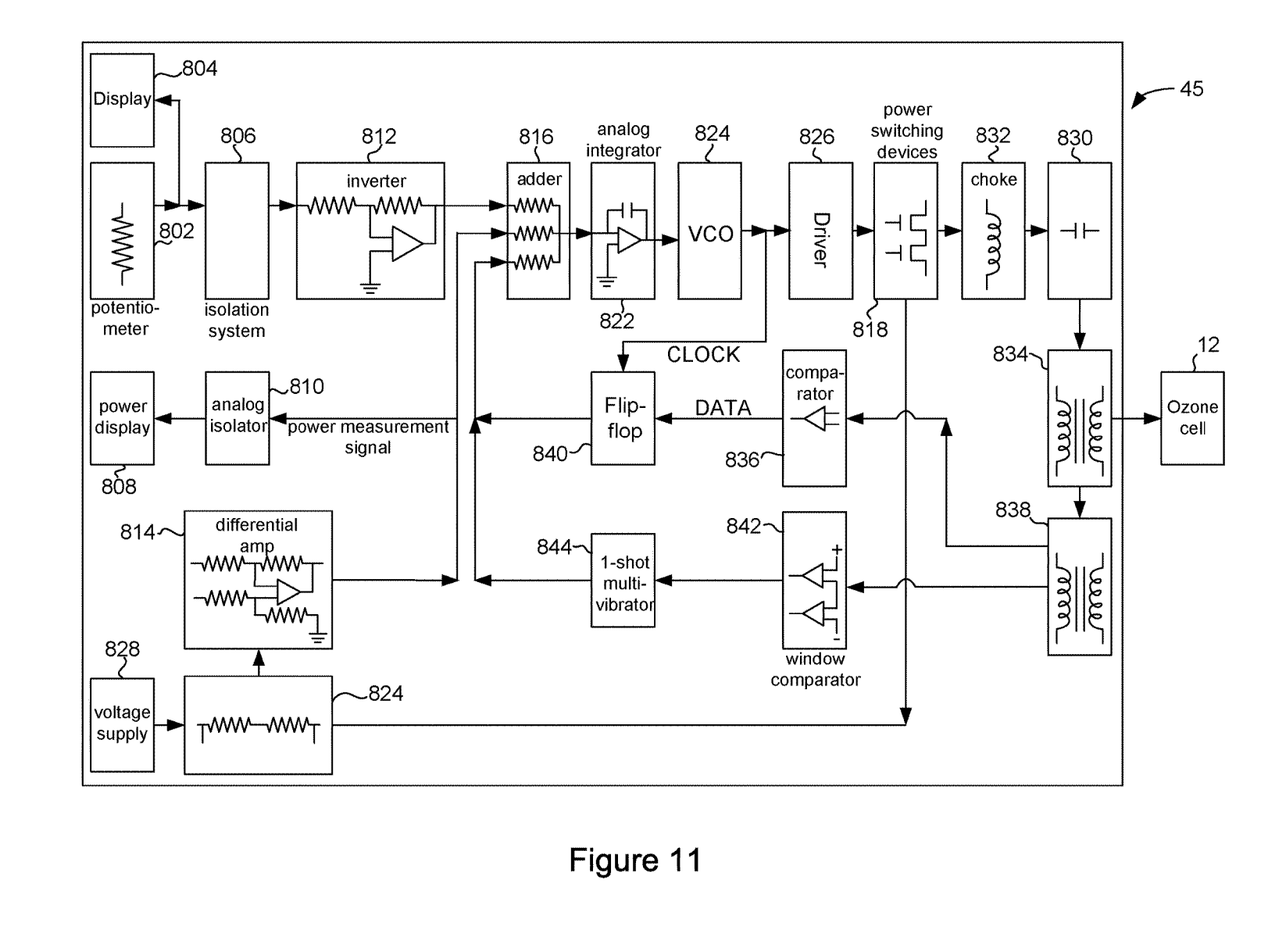
FIG. 11 is a more detailed schematic illustration of the FIG. 9 power supply according to an embodiment of the present invention.

FIG. 11 is a schematic illustration of another embodiment the power supply 45 for the corona discharge cell 12. The power supply 12 includes a potentiometer 802 with a display 804 (e.g., a bar graph) of the power setting. The output of the potentiometer 802 passes through an electrical isolation system 806 for safety. The power supply 12 also includes a power display 808 connected to an analog isolator 810, the input of which is the power measurement signal.

The control signal from the potentiometer 802 is inverted in an inverter 812 and then summed with the output of a differential amplifier 814 in an adder 816. The output of the differential amplifier 814 is a measure of the average DC current supplied to the power switching devices 818. Because DC voltage is constant and since the switching devices operate with high efficiency, the average current is an analog of the rate of energy delivery to the ozone cell 12. By virtue of the inversion of control from the potentiometer 802, the output of the adder 816 (i.e., summing circuit) may be considered to be the difference between the control signal and the rate of energy delivery delivered to the cell 12. The difference may also be considered to be an error signal.

The error signal is integrated by an analog integrator 822 (i.e., time integral) whose output control frequency in a voltage-controlled oscillator (VCO) 824. It should be noted that use of an integrator here is just a special case of a Proportion Integral Derivative (PID) control loop. In this case, it is convenient and simplest to make the proportional and the derivative components to be zero, but they could be set differently without significantly affecting the operation. The output of the VCO 824 controls a switching device drive circuit 826. The effect is that the DC power from the medium voltage supply 828 is converted into a square wave at the frequency of the voltage controlled oscillator 824 through a current sensing resistor. The DC component is removed by a series capacitor 830. The output also passes through a choke 832 and a step-up transformer 834 whose output is applied to the ozone cell 12. In one embodiment, the switching device drive circuit 826 may comprise a MOSFET half-bridge drive circuit. In another embodiment, the switching device drive circuit 826 may comprise a MOSFET fullbridge drive circuit.

The ozone cell 12 presents a load with a large capacitive element. That is to say, current phase leads voltage phase. The reflected capacitance forms a resonant circuit in combination with the choke 832. Frequency of operation is kept above the resonance frequency. As frequency decreases, power supplied to the ozone cell 12 increases, and correspondingly as frequency increases, applied power decreases. The aforementioned error changes the frequency of the voltage controlled oscillator 834 in a direction that tends to reduce error.

The input power to the switching devices 818 is a good estimate of the rate of energy delivered to the ozone cell 12. That is because the switching devices dissipate little power, the capacitor 830 and choke 832 are reactive, therefore generating no heat, and the transformer 834 is efficient. The only significant power dissipated within the cell is within the corona discharge in the cell 12. Power dissipated in the corona discharge is precisely the quantity we wish to control.

It should be noted that if frequency were to go lower than resonance, the negative feedback loop would become an unstable positive feedback loop, a possibility to be excluded. This case can be identified by looking at the relative phase of current and voltage. A comparator 836 connected to the current transformer 838 indicates the sign of current on a continuous basis. When voltage goes positive, the state at that time is latched into the flip flop 840. If the output of the flip-flop 840 goes high, indicating frequency at or below resonance, the integrator 822 is driven in a direction that increases frequency, preventing operation below the resonant frequency. Similarly, there is over-current detection consisting of a window comparator 842 and a one-shot multivibrator 844. If the current magnitude exceeds a set point, the integrator 822 is driven to a higher frequency for the duration of the one-shot multivibrator 844 pulse.

Higher frequency decreases current because at higher frequencies (so long as operation is above resonance) the impedance of the choke 832 is higher, and therefore also the impedance of the load presented to the switching devices 818 by the combination of choke 832, capacitor 830, transformer 834, and ozone cell 12. Further description of power supplies for a corona discharge cell for an ozone generation system is found in U.S. patent application Ser. No. 14/849,659, filed Sep. 10, 2013 and published Dec. 31, 2015, Pub. No. 2015/0376006, which is incorporated by reference for all purposes.

Thus the described ozone generation system which is easily adaptable for different medium and small process applications can be constructed from inexpensive parts; the system can be manufactured with relatively low costs. Operation of the system is accurate and stable under easy human operator control.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. An ozone generation system for supplying ozone to an application process, the system comprising:
    a source of feed gas;
    a corona discharge cell receiving the feed gas from the feed gas source and generating ozone for the application process;
    a flow controller measuring and managing the flow of the feed gas from the feed gas source to the corona discharge cell, the controller including
        a first valve controlling the flow from the feed gas source to the corona discharge cell, the valve responsive to electrical control signals;
        an orifice through which the feed gas flows;
        a first pressure transducer measuring a differential gas pressure across the orifice and at intervals measuring a zero differential pressure to recalibrate the first pressure transducer;
        a second pressure transducer measuring the corona discharge cell pressure;
        a temperature transducer measuring temperature of the gas flow at the orifice; and
        an electronics system adjusting the first valve to maintain a constant flow from the feed gas source to the corona discharge cell, the electronics system generating the electrical control signals from calculations of flow of the feed gas through the orifice responsive to electrical signals from the first pressure transducer, the second pressure transducer and the temperature transducer; and
    a regulator maintaining pressure in the corona discharge cell independent of pressure in the application process.

2. The ozone generation system of claim 1 wherein the electronics system sends the electrical control signals to the first valve responsive to the calculations of flow of the feed gas through the orifice to control the flow of the feed gas to the corona discharge cell.

3. The ozone generation system of claim 2 wherein the flow controller further comprises:
    a second valve having a first pneumatic connection to the flow of feed gas before the orifice, a second pneumatic connection to the flow of feed gas after the orifice and a third pneumatic connection to a first input of the first pressure transducer, the first pressure transducer also having a second input connected to the second pneumatic connection, the second valve controllably connecting the first and second inputs of the first pressure transducer to the first and second pneumatic connections respectively and connecting the first and second inputs of the first pressure transducer to the second pneumatic connection responsive to the electrical control signals.

4. The ozone generation system of claim 3 wherein the electronics system transmits the electrical control signals to the second valve so that at intervals at the first and second inputs of the first pressure transducer are both connected to the second pneumatic connection to measure a zero differential pressure for a recalibration of the first pressure transducer.

5. The ozone generation system of claim 4 wherein the electronics system stores a zero differential pressure measurement value and subtracts the zero differential pressure measurement value from subsequent pressure measurement values from the first pressure transducer.

6. An ozone generation system for supplying ozone to an application process, the system comprising:
    a source of feed gas;
    a corona discharge cell receiving the feed gas from the feed gas source and generating ozone for the application process;
    a flow controller measuring and managing the flow of the feed gas from the feed gas source to the corona discharge cell; and a regulator receiving gas from the corona discharge cell and sending the gas to the application process, the regulator further comprising:
   a block with an inlet for receiving gas from the corona discharge cell and an outlet for sending the gas to the application process;
   a flexible diaphragm disposed with respect to the block to cover the inlet and outlet; and
   a subsystem biasing the diaphragm against the inlet and outlet by gas pressure so that the pressure of the gas flow from the inlet to the outlet is controlled by the gas pressure of the subsystem against the diaphragm;
   whereby the regulator maintains pressure in the corona discharge cell independent of pressure in the application process.

7. The ozone generation system of claim 6 wherein the diaphragm biasing subsystem of the regulator further comprises:
   a second gas source and a second pressure regulator in pneumatic communication with the diaphragm, the pressure regulator setting the gas pressure against the diaphragm to control the pressure of the gas flow from the inlet to the outlet.

8. The ozone generation system of claim 7 wherein the second gas source and second pressure regulator are in pneumatic communication with the diaphragm through a base of a T junction with first and second arms, the first arm connected to the second gas source and second pressure regulator, and the second arm directly connected to ambient air through a second orifice.

9. The ozone generation system of claim 6 wherein the diaphragm biasing subsystem of the regulator further comprises:
   a chamber in pneumatic communication with the diaphragm;
   a third valve controlling the supply of gas from a source to the chamber, the gas creating pressure in the chamber and against the diaphragm; and
   a fourth valve controlling the removal of gas from the chamber;
   whereby operation of the third and fourth valves control the gas pressure of the subsystem against the diaphragm.

10. The ozone generation system of claim 9 wherein the diaphragm biasing subsystem of the regulator further comprises a pressure transducer in pneumatic communication with the chamber, the pressure transducer providing an electrical signal to control the operation of the third and fourth valves responsive to the gas pressure of the subsystem against the diaphragm.

11. The ozone generation system of claim 6 wherein the flow controller further comprises;
   a first valve controlling the flow from the feed gas source to the corona discharge cell, the valve responsive to electrical control signals; and
   an electronics system adjusting the valve to maintain a constant flow from the feed gas source to the corona discharge cell, the electronics system generating the electrical control signals responsive to calculations of flow of the feed gas through an orifice.

12. An ozone generation system for supplying ozone to an application process, the system comprising:
   a source of feed gas;
   a corona discharge cell receiving the feed gas from the feed gas source and generating ozone for the application process;
   a flow controller measuring and managing the flow of the feed gas from the feed gas source to the corona discharge cell; and
   a regulator receiving gas from the corona discharge cell and sending the gas to the application process, the regulator further comprising:
      a block with an inlet for receiving gas from the corona discharge cell and an outlet for sending the gas to the application process, the block having a chamber in pneumatic connection with the inlet;
      a flexible diaphragm disposed with respect to the block to cover the outlet and the chamber; and
      a sliding piston biasing the diaphragm against the outlet so that pressure of the gas in the chamber from the inlet on one side of the diaphragm and the bias of the sliding piston and ambient pressure on an opposite side of the diaphragm controls the pressure of the gas flow from the inlet to the outlet;
   whereby the regulator maintains pressure in the corona discharge cell independent of application process pressure.

13. The ozone generation system of claim 12 in which the sliding piston of the regulator maintaining pressure is biased by a spring force.

14. The ozone generation system of claim 13 in which regulator maintaining pressure varies the pressure of the gas flow from the inlet to the outlet by varying the spring force.

15. The ozone generation system of claim 12 wherein the flow controller further comprises;
   a first valve controlling the flow from the feed gas source to the corona discharge cell, the valve responsive to electrical control signals; and
   an electronics system adjusting the valve to maintain a constant flow from the feed gas source to the corona discharge cell, the electronics system generating the electrical control signals responsive to calculations of flow of the feed gas through an orifice.

16. A flow controller for measuring and managing flow of a feed gas from a feed gas source to a corona discharge cell in an ozone generation system, comprising:
   a first valve controlling the flow from the feed gas source to the corona discharge cell, the valve responsive to electrical control signals;
   an orifice through which the feed gas flows; and
   a first pressure transducer measuring a differential gas pressure across the orifice and at intervals measuring a zero differential pressure to recalibrate the first pressure transducer;
   a second pressure transducer measuring a corona discharge cell pressure;
   a temperature transducer measuring temperature of the gas flow at the orifice; and
   an electronics system adjusting the first valve to maintain a constant flow from the feed gas source to the corona discharge cell, the electronics system generating the electrical control signals from calculations of flow of the feed gas through the orifice responsive to electrical signals from the first pressure transducer, the second pressure transducer and the temperature transducer.

17. The flow controller of claim 16 wherein the electronics system sends the electrical control signals to the first valve responsive to the calculations of flow of the feed gas through the orifice to control the flow of the feed gas to the corona discharge cell.

18. The flow controller of claim 17 further comprising:
   a second valve having a first pneumatic connection to the flow of feed gas before the orifice, a second pneumatic connection to the flow of feed gas after the orifice and a third pneumatic connection to a first input of the first pressure transducer, the first pressure transducer also having a second input connected to the second pneumatic connection, the second valve controllably connecting the first and second inputs of the first pressure transducer to the first and second pneumatic connections respectively and connecting the first and second inputs of the first pressure transducer to the second pneumatic connection responsive to the electrical control signals.

19. The flow controller of claim 18 wherein the electronics system transmits the electrical control signals to the second valve so that at intervals at the first and second inputs of the first pressure transducer are both connected to the second pneumatic connection to measure a zero differential pressure for a recalibration of the first pressure transducer.

20. The flow controller of claim 19 wherein the electronics system stores a zero differential pressure measurement value and subtracts the zero differential pressure measurement value from subsequent pressure measurement values from the first pressure transducer.

21. A pressure regulator for receiving gas from a corona discharge cell and sending the gas to an application process for an ozone generation system, comprising:
a block with an inlet for receiving gas from the corona discharge cell and an outlet for sending the gas to the application process;
a flexible diaphragm disposed with respect to the block to cover the inlet and outlet; and
a subsystem biasing the diaphragm against the inlet and outlet by gas pressure so that the pressure of the gas flow from the inlet to the outlet is controlled by the gas pressure of the subsystem against the diaphragm;
whereby the regulator maintains pressure in the corona discharge cell independent of pressure in the application process.

22. The pressure regulator of claim 21 wherein the diaphragm biasing subsystem of the regulator further comprises:
a second gas source and a second pressure regulator in pneumatic communication with the diaphragm, the pressure regulator setting the gas pressure against the diaphragm to control the pressure of the gas flow from the inlet to the outlet.

23. The pressure regulator of claim 22 wherein the second gas source and second pressure regulator are in pneumatic communication with the diaphragm through a base of a T junction with first and second arms, the first arm connected to the second gas source and second pressure regulator, and the second arm directly connected to ambient air through a second orifice.

24. The pressure regulator of claim 21 wherein the diaphragm biasing subsystem of the regulator further comprises:
a chamber in pneumatic communication with the diaphragm;
a third valve controlling the supply of gas from a source to the chamber, the gas creating pressure in the chamber and against the diaphragm; and
a fourth valve controlling the removal of gas from the chamber;
whereby operation of the third and fourth valves control the gas pressure of the subsystem against the diaphragm.

25. The pressure regulator of claim 24 wherein the diaphragm biasing subsystem of the regulator further comprises a pressure transducer in pneumatic communication with the chamber, the pressure transducer providing an electrical signal to control the operation of the third and fourth valves responsive to the gas pressure of the subsystem against the diaphragm.

26. A pressure regulator for receiving gas from a corona discharge cell and sending the gas to an application process for an ozone generation system, the pressure regulator comprising:
a block with an inlet for receiving gas from the corona discharge cell and an outlet for sending the gas to the application process, the block having a chamber in pneumatic connection with the inlet;
a flexible diaphragm disposed with respect to the block to cover the outlet and the chamber; and
a sliding piston biasing the diaphragm against the outlet so that pressure of the gas in the chamber from the inlet on one side of the diaphragm and the bias of the sliding piston and ambient pressure on an opposite side of the diaphragm controls the pressure of the gas flow from the inlet to the outlet;
whereby the regulator maintains pressure in the corona discharge cell independent of application process pressure.

27. The pressure regulator of claim 26 wherein the sliding piston of the regulator maintaining pressure is biased by a spring force.

28. The pressure regulator of claim 27 wherein the regulator varies the pressure of the gas flow from the inlet to the outlet by varying the spring force.

* * * * *